(12) United States Patent
Williamson

(10) Patent No.: US 11,399,971 B2
(45) Date of Patent: Aug. 2, 2022

(54) INTRALUMINAL DEVICE WITH IMPROVED FLEXIBILITY AND DURABILITY

(75) Inventor: Michael V. Williamson, Clayton, CA (US)

(73) Assignee: CARDINAL HEALTH SWITZERLAND 515 GMBH, Bar Zug (CH)

( * ) Notice: Subject to any disclaimer, the term of this patent is extended or adjusted under 35 U.S.C. 154(b) by 1433 days.

(21) Appl. No.: 12/913,896

(22) Filed: Oct. 28, 2010

(65) Prior Publication Data
US 2011/0106238 A1 May 5, 2011

Related U.S. Application Data

(60) Provisional application No. 61/256,633, filed on Oct. 30, 2009.

(51) Int. Cl.
*A61F 2/82* (2013.01)
*A61F 2/966* (2013.01)
*A61F 2/915* (2013.01)

(52) U.S. Cl.
CPC .............. *A61F 2/966* (2013.01); *A61F 2/915* (2013.01); *A61F 2002/91558* (2013.01);
(Continued)

(58) Field of Classification Search
CPC ..................................... A61F 2/06; A61F 2/82
(Continued)

(56) References Cited

U.S. PATENT DOCUMENTS

| | | |
|---|---|---|
| 3,585,707 A | 6/1971 | Stevens |
| 4,665,771 A | 5/1987 | Mitchell |

(Continued)

FOREIGN PATENT DOCUMENTS

| | | |
|---|---|---|
| CA | 2459914 A1 | 3/2003 |
| CN | 1691924 A1 | 2/2005 |

(Continued)

OTHER PUBLICATIONS

Notice of Preliminary Rejection in corresponding Korean Patent Application 10-2012-7013585, dated Feb. 28, 2017, 6 pages.

(Continued)

*Primary Examiner* — Matthew W Schall
(74) *Attorney, Agent, or Firm* — Arentfox Schiff LLP

(57) ABSTRACT

In accordance with the present invention, there is provided a stent for insertion into a vessel of a patient. The stent is a tubular member having front and back open ends and a longitudinal axis extending there between. The tubular member has a first smaller diameter for insertion into a patient and navigation through the vessels, and a second larger diameter for deployment into the target area of a vessel. The tubular member is made from a plurality of adjacent hoops extending between the front and back ends. The hoops include a plurality of longitudinal struts and a plurality of loops connecting adjacent struts. The stent further includes a plurality of bridges having loop to bridge connections which connect adjacent hoops to one another. The bridge to loop connection points are separated angularly with respect to the longitudinal axis. The bridges have one end attached to a loop, another end attached to a loop on an adjacent hoop. The connection point between the bridge and the hoops will have a repeating pattern over a plurality of strut apices such that the benefits of a decreased number of bridges is realized while simultaneously avoiding the creation of overly unconstrained hoops. It is preferred that the ratio of total number of circumferentially aligned loops to the number of loops spanned by a particular bridge be a whole number.

13 Claims, 14 Drawing Sheets

(52) U.S. Cl.
CPC . *A61F 2210/0076* (2013.01); *A61F 2230/005* (2013.01); *A61F 2230/0054* (2013.01); *A61F 2250/0036* (2013.01)

(58) Field of Classification Search
USPC ..................................................... 623/1.16
See application file for complete search history.

(56) References Cited

U.S. PATENT DOCUMENTS

| | | |
|---|---|---|
| 4,665,905 A | 5/1987 | Brown |
| 4,665,906 A | 5/1987 | Jervis |
| 4,733,665 A | 3/1988 | Palmaz |
| 4,925,445 A | 5/1990 | Sakamoto et al. |
| 5,045,072 A | 9/1991 | Castillo et al. |
| 5,104,404 A | 4/1992 | Wolff |
| 5,254,107 A | 10/1993 | Soltesz |
| 5,397,335 A | 3/1995 | Gresi et al. |
| 5,383,892 A | 6/1995 | Cardon et al. |
| 5,449,373 A | 9/1995 | Pinchasik et al. |
| 5,683,441 A | 11/1997 | Kavteladze et al. |
| 5,776,161 A | 7/1998 | Globerman et al. |
| 5,807,404 A | 9/1998 | Richter |
| 5,824,059 A | 10/1998 | Wijay |
| 5,830,179 A | 11/1998 | Mikus et al. |
| 5,868,781 A | 2/1999 | Killion |
| 5,876,449 A | 3/1999 | Starck et al. |
| 5,911,754 A | 6/1999 | Kamesaka et al. |
| 5,913,895 A | 6/1999 | Burpee et al. |
| 6,019,778 A | 2/2000 | Wilson et al. |
| 6,042,606 A | 3/2000 | Frantzen |
| 6,129,755 A | 10/2000 | Mathis |
| 6,190,406 B1 | 2/2001 | Duerig et al. |
| 6,203,569 B1 | 3/2001 | Wijay |
| 6,342,067 B1 | 1/2002 | Mathis |
| 6,416,543 B1 | 7/2002 | Hilaire et al. |
| 6,589,276 B2 | 7/2003 | Pinchasik et al. |
| 7,131,993 B2 | 11/2006 | Gregorich |
| 7,179,286 B2 | 2/2007 | Lenz |
| 2002/0143386 A1 | 10/2002 | Davila et al. |
| 2006/0030930 A1 | 2/2006 | Burgermeister et al. |
| 2006/0129230 A1 | 6/2006 | Gregorich |
| 2007/0150050 A1 | 6/2007 | Lenz |
| 2008/0065195 A1 | 3/2008 | Brown et al. |
| 2008/0294238 A1* | 11/2008 | Tischler et al. ............. 623/1.16 |

FOREIGN PATENT DOCUMENTS

| | | |
|---|---|---|
| EP | 0491349 B1 | 6/1992 |
| EP | 0686379 B1 | 12/1995 |
| EP | 0540290 B1 | 1/1998 |
| EP | 0884029 B1 | 12/1998 |
| EP | 0928606 B1 | 1/1999 |
| EP | 1190685 A2 | 3/2002 |
| EP | 1523960 A2 | 4/2005 |
| EP | 2478876 A1 | 7/2012 |
| FR | 2764794 A | 6/1997 |
| JP | 2002-530146 A | 9/2002 |
| JP | 2005-118571 A | 5/2005 |
| JP | 2008-511423 A | 4/2006 |
| WO | WO 95/31945 A1 | 11/1995 |
| WO | WO 96/26689 A1 | 9/1996 |
| WO | WO 97/00294 A1 | 1/1997 |
| WO | WO 97/40781 A1 | 11/1997 |
| WO | WO 97/40783 A2 | 11/1997 |
| WO | WO 98/20810 A1 | 5/1998 |
| WO | WO 98/40035 A1 | 9/1998 |
| WO | 2000/030563 | 6/2000 |
| WO | 2004/028571 A2 | 8/2004 |
| WO | WO 2004/084769 A2 | 10/2004 |
| WO | 2006005026 A2 | 1/2006 |
| WO | 2006/026777 A2 | 3/2006 |
| WO | 2009/014888 A1 | 1/2009 |

OTHER PUBLICATIONS

Reexamination Decision dated Dec. 26, 2016, in corresponding Chinese Patent Application No. 201080050418.3, 11 pages.
Office Action dated Sep. 7, 2016, in corresponding Canadian Patent Application No. 2,779,080, 3 pages.
Examination Report for corresponding European Patent Application No. 10779118.8 dated Sep. 12, 2017, pp. 1-5.
Decision of Refusal in Japanese Patent Application No. 2012537056, dated Feb. 23, 2016, and translation thereof.
Decision of Refusal in Japanese Patent Application No. 2012537056, dated Feb. 17, 2015, and translation thereof.
Decision of Refusal in Japanese Patent Application No. 2012537056, dated Jul. 1, 2014, and translation thereof.
International Search Report in International Patent Application No. PCT/US2010/054455, dated May 5, 2011.
Written Opinion in International Patent Application No. PCT/US2010/054455, dated Apr. 30, 2012.
International Preliminary Report on Patentability in International Patent Application No. PCT/US2010/054455, dated May 1, 2012.
First Office Action in Chinese Patent Application No. 201080050418.3, dated May 5, 2014, and translation thereof.
Third Office Action in Chinese Patent Application No. 201080050418.3, dated May 18, 2015, and translation thereof.
First Office Action in Chinese Patent Application No. 201710166078.4, dated Dec. 29, 2017, and translation thereof.
Notification to Grant Patent in Chinese Patent Application No. 201710166078.4, dated Mar. 22, 2019, and translation thereof.
Communication in European Patent Application No. 10779118.8, dated Nov. 14, 2019.
Notice of Final Rejection in Korean Patent Application No. 10-2012-7013585, dated Sep. 7, 2017, and translation thereof.
Grant of Patent in Korean Patent Application No. 10-2012-7013585, dated Mar. 20, 2018, and translation thereof.
Chinese Office Action and Translation of Text dated Dec. 3, 2014 for CN Appln. No. 201080050418.3.

* cited by examiner

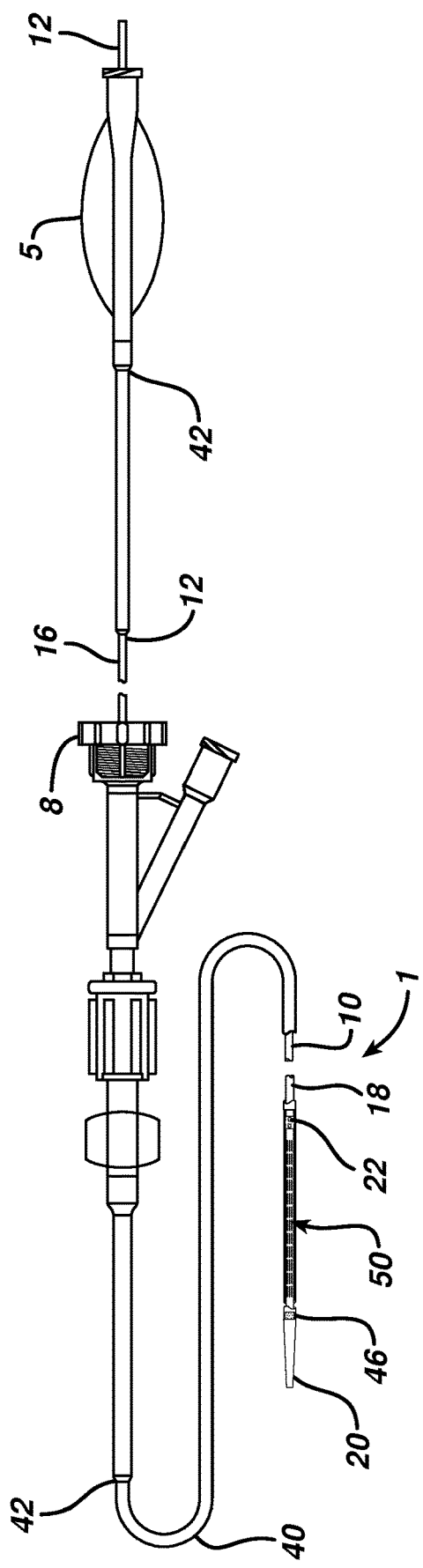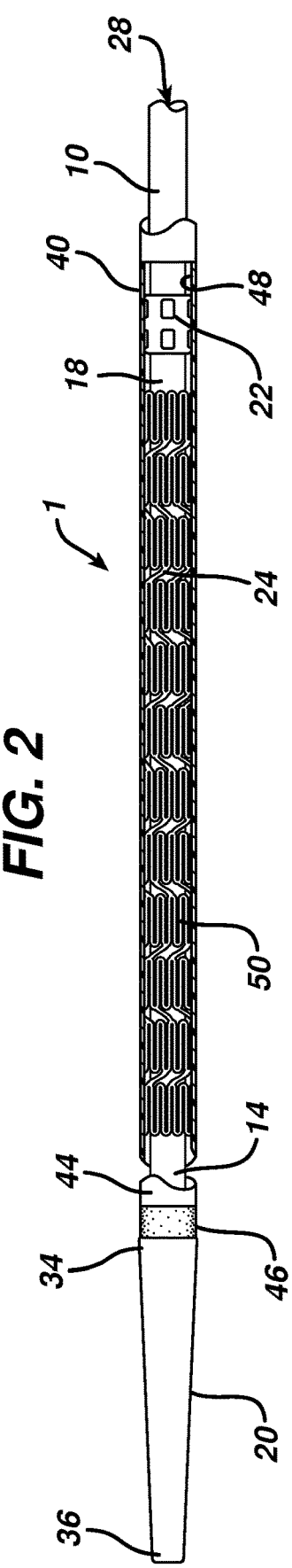

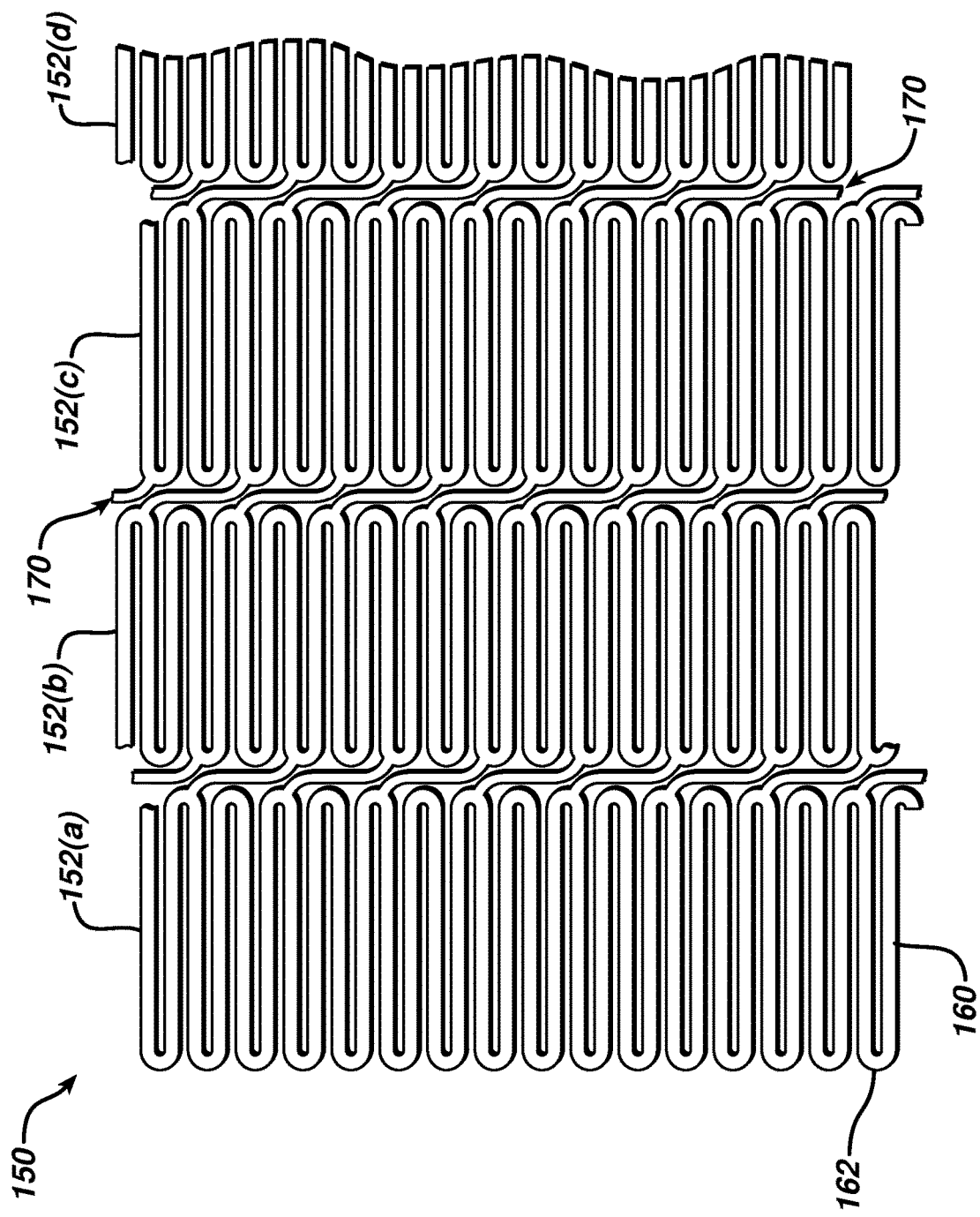

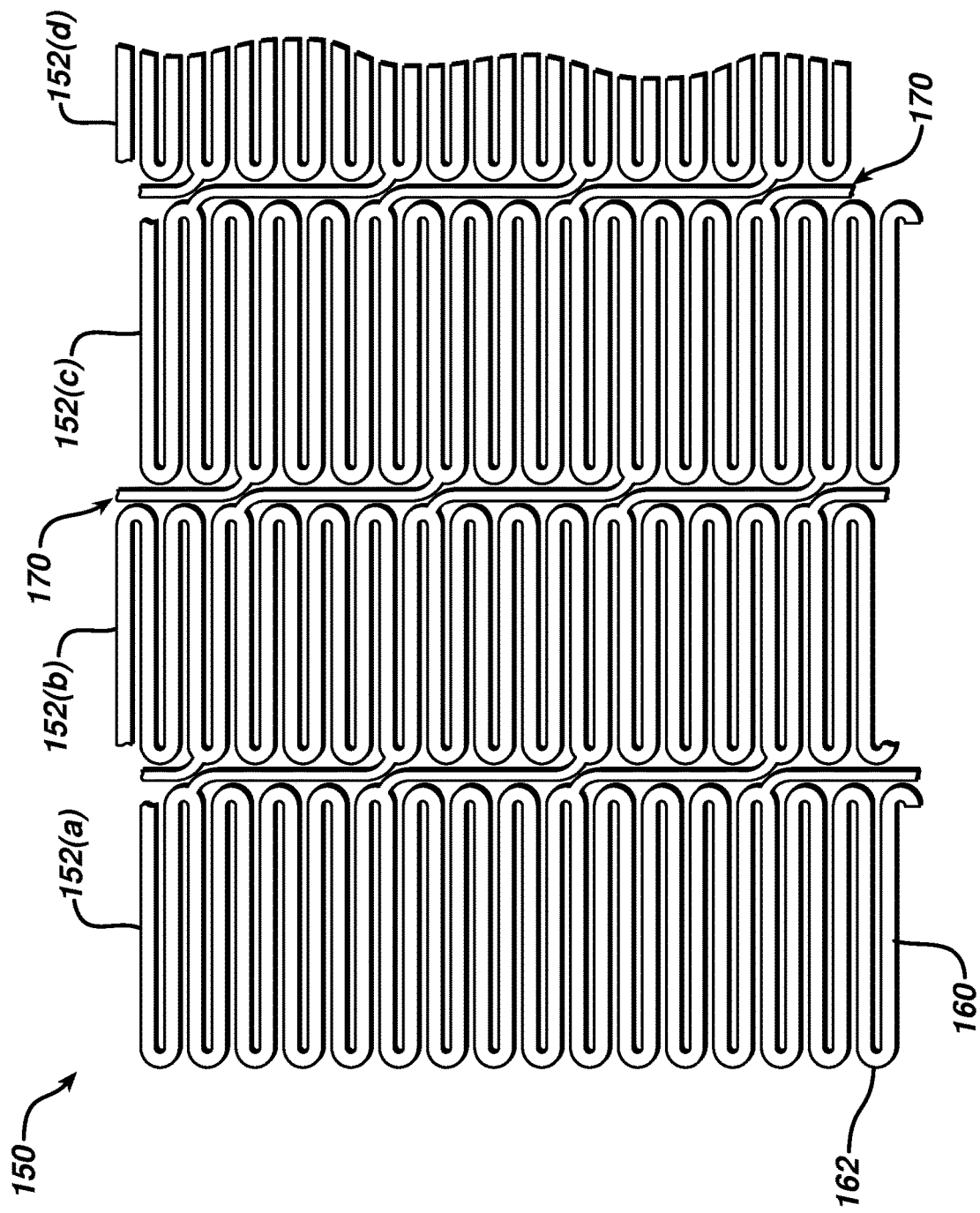

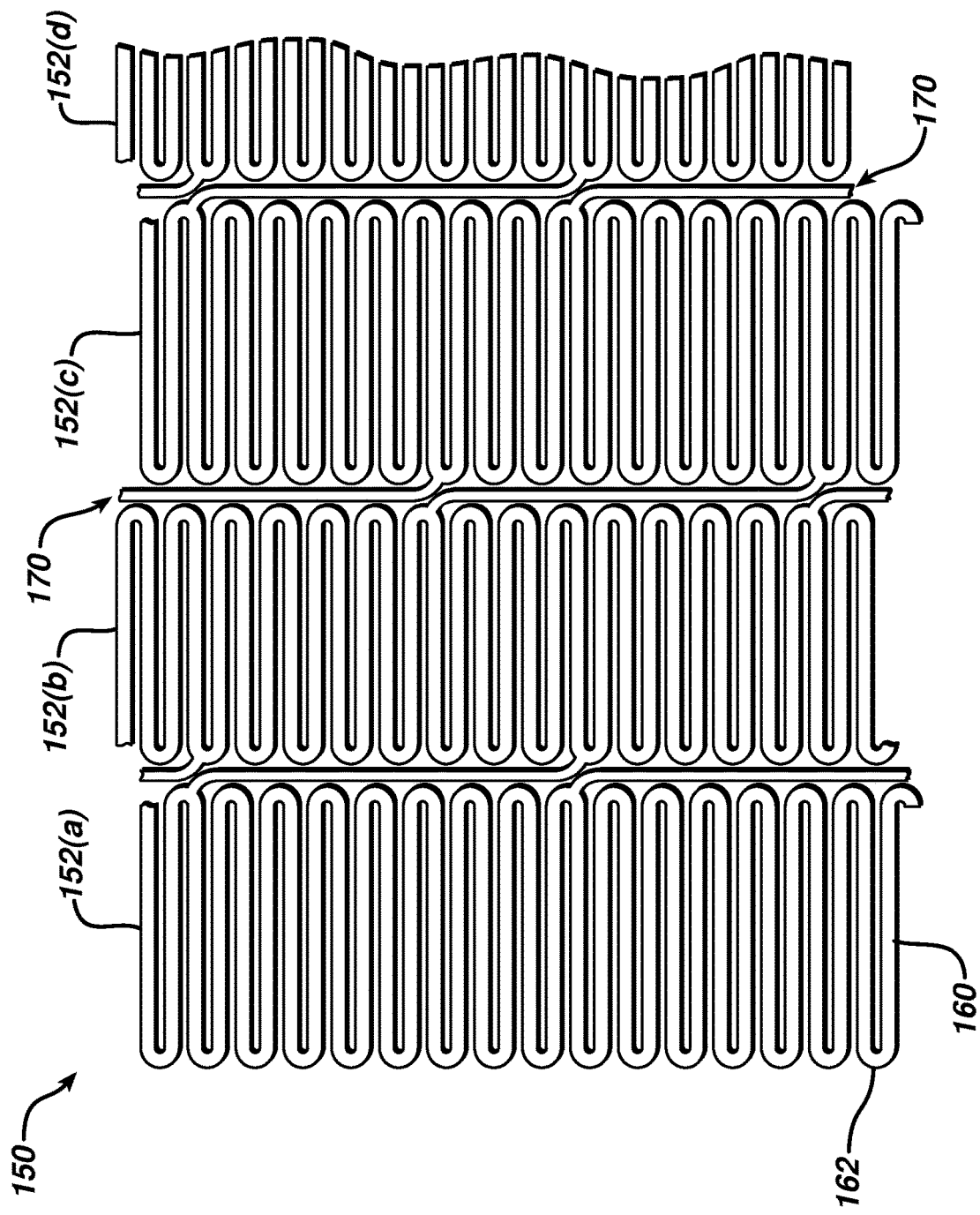

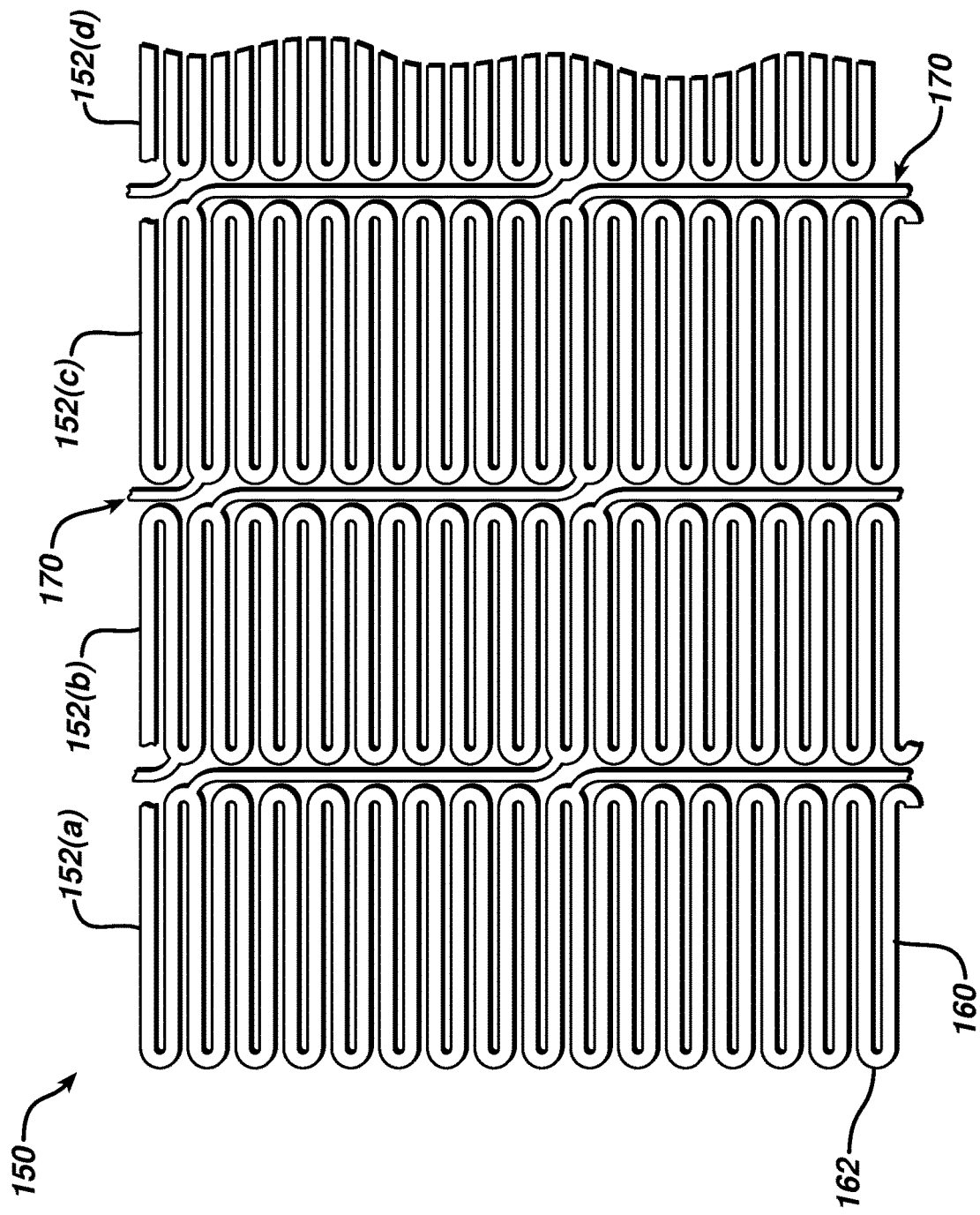

INTRALUMINAL DEVICE WITH IMPROVED FLEXIBILITY AND DURABILITY

CROSS REFERENCE TO RELATED APPLICATION

This application claims the benefit of U.S. Provisional Application Ser. No. 61/256,633 filed Oct. 30, 2009, which is incorporated by reference herein.

FIELD OF THE INVENTION

The present invention relates to an expandable intraluminal grafts ("stents") for use within a body passageway or duct which are particularly useful for repairing blood vessels narrowed or occluded by disease. The present invention relates even further to such stents which are self-expanding and made from a superelastic material such as Nitinol. The present invention also relates to delivery systems for such stents.

BACKGROUND OF THE INVENTION

Percutaneous transluminal coronary angioplasty (PTCA) is a therapeutic medical procedure used to increase blood flow through the coronary artery and can often be used as an alternative to coronary by-pass surgery. In this procedure, the angioplasty balloon is inflated within the stenosed vessel, or body passageway, in order to shear and disrupt the wall components of the vessel to obtain an enlarged lumen. With respect to arterial stenosed lesions, the relatively incompressible plaque remains unaltered, while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen.

Typically, the distending intraluminal pressure within the body passageway can hold the disrupted layer, or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, immediate surgery is necessary to correct this problem.

Recently, transluminal prostheses have been widely used in the medical arts for implantation in blood vessels, biliary ducts, or other similar organs of the living body. These prostheses are commonly known as stents and are used to maintain, open, or dilate tubular structures. An example of a commonly used stent is given in U.S. Pat. No. 4,733,665 filed by Palmaz on Nov. 7, 1985, which is hereby incorporated herein by reference. Such stents are often referred to as balloon expandable stents. Typically the stent is made from a solid tube of stainless steel. Thereafter, a series of cuts are made in the wall of the stent. The stent has a first smaller diameter which permits the stent to be delivered through the human vasculature by being crimped onto a balloon catheter. The stent also has a second, expanded diameter, upon the application, by the balloon catheter, from the interior of the tubular shaped member of a radially, outwardly extending.

However, such stents are often impractical for use in some vessels such as the carotid artery. The carotid artery is easily accessible from the exterior of the human body, and is often visible by looking at ones neck. A patient having a balloon expandable stent made from stainless steel or the like, placed in their carotid artery might be susceptible to sever injury through day to day activity. A sufficient force placed on the patient's neck, such as by falling, could cause the stent to collapse, resulting in injury to the patient. In order to prevent this, self expanding stents have been proposed for use in such vessels. Self expanding stents act like springs and will recover to their expanded or implanted configuration after being crushed.

One type of self-expanding stent is disclosed in U.S. Pat. No. 4,665,771, which stent has a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a "braided stent" and is so designated herein. Placement of such stents in a body vessel can be achieved by a device which comprise an outer catheter for holding the stent at its distal end, and an inner piston which pushes the stent forward once it is in position.

However, braided stents have many disadvantages. They typically do not have the necessary radial strength to effectively hold open a diseased vessel. In addition, the plurality of wires or fibers used to make such stents could become dangerous if separated from the body of the stent, where it could pierce through the vessel. Therefore, there has been a desire to have a self-expanding stent, which is cut from a tube of metal, which is the common manufacturing method for many commercially available balloon expandable stents. In order to manufacture a self-expanding stent cut from a tube, the alloy used would preferably be superelastic or psuedoelastic characteristics at body temperature, so that it is crush recoverable.

The prior art makes reference to the use of alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original un-deformed shape by the transformation back to the original phase.

Alloys having shape memory/superelastic characteristics generally have at least two phases. These phases are a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable (the Af temperature). The shape of the metal during this heat treatment is the shape "remembered". The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase to transform to the austenite phase and during this phase transformation the metal reverts back to its original shape if unrestrained. If restrained, the metal will remain martensitic until the restraint is removed.

Methods of using the shape memory characteristics of these alloys in medical devices intended to be placed within a patient's body present operational difficulties. For example, with shape memory alloys having a stable martensite temperature below body temperature, it is frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices can be introduced into a patient's body with little or no problem, but they must be heated to the martensite-to-austenite transformation temperature which is frequently high enough to cause tissue damage and very high levels of pain.

When stress is applied to a specimen of a metal such as Nitinol exhibiting superelastic characteristics at a temperature above which the austenite is stable (i.e. the temperature at which the transformation of martensite phase to the austenite phase is complete), the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation. The martensitic metal first deforms elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity. It is this property of the material which makes it useful in manufacturing tube cut self-expanding stents. The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

However, the prior art has yet to disclose any suitable tube cut self expanding stents. In addition, many of the prior art stents lacked the necessary rigidity or hoop strength to keep the body vessel open. In addition, many of the prior art stents have large openings at their expanded diameter. The smaller the openings are on an expanded stent, the more plaque or other deposits it can trap between the stent and the vessel wall. Trapping these deposits is important to the continuing health of the patient in that it helps prevent strokes as well as helps prevents restenosis of the vessel it is implanted into. The present invention provides for a selfexpanding tube cut stent which overcomes many of the disadvantages associated with the prior art stents.

SUMMARY OF THE INVENTION

In accordance with the present invention, there is provided a stent for insertion into a vessel of a patient. The stent is a tubular member having front and back open ends and a longitudinal axis extending therebetween. The tubular member has a first smaller diameter for insertion into a patient and navigation through the vessels, and a second larger diameter for deployment into the target area of a vessel. The tubular member is made from a plurality of adjacent hoops extending between the front and back ends. The hoops include a plurality of longitudinal struts and a plurality of loops connecting adjacent struts. The stent further includes a plurality of bridges having loop to bridge connections which connect adjacent hoops to one another. The bridge to loop connection points are separated angularly with respect to the longitudinal axis. The bridges have one end attached to a loop, another end attached to a loop on an adjacent hoop. The bridges have a non-linear curved profile between their bridge to loop connection points.

BRIEF DESCRIPTION OF DRAWINGS

The foregoing and other aspects of the present invention will best be appreciated with reference to the detailed description of the invention in conjunction with the accompanying drawings, wherein:

FIG. 1 is a simplified partial cross-sectional view of a stent delivery apparatus having a stent loaded therein, which can be used with a stent made in accordance with the present invention.

FIG. 2 is a view similar to that of FIG. 1 but showing an enlarged view of the distal end of the apparatus.

FIG. 7A is a view similar to that of FIG. 4 but showing an alternative embodiment of the present invention.

FIG. 7B is a view similar to that of FIG. 4 but showing an alternative embodiment of the present invention.

FIG. 7C is a view similar to that of FIG. 4 but showing an alternative embodiment of the present invention.

FIG. 7F is a view similar to that of FIG. 4 but showing an alternative embodiment of the present invention.

DETAILED DESCRIPTION OF THE INVENTION

Figure 3:
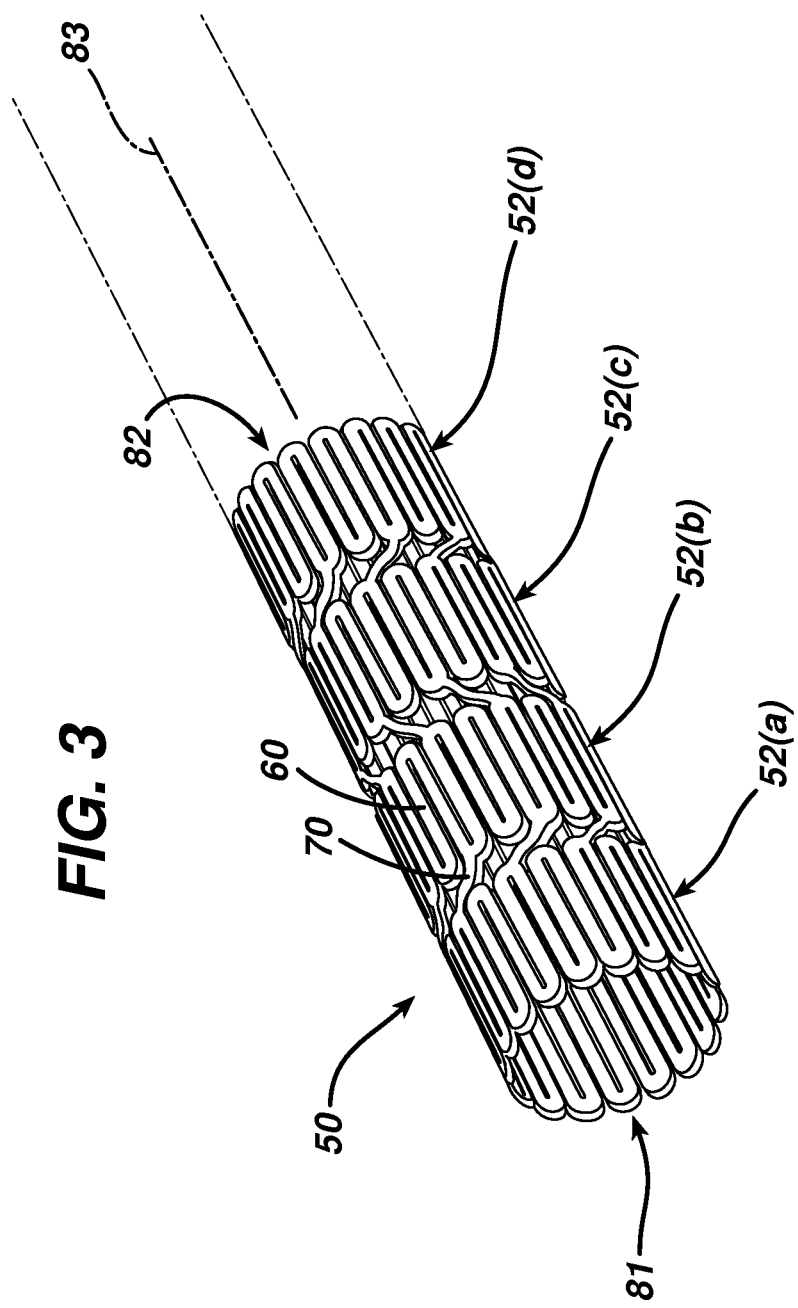
FIG. 3 is a perspective view of a stent made in accordance with the present invention, showing the stent in its compressed state.
Figure 4:
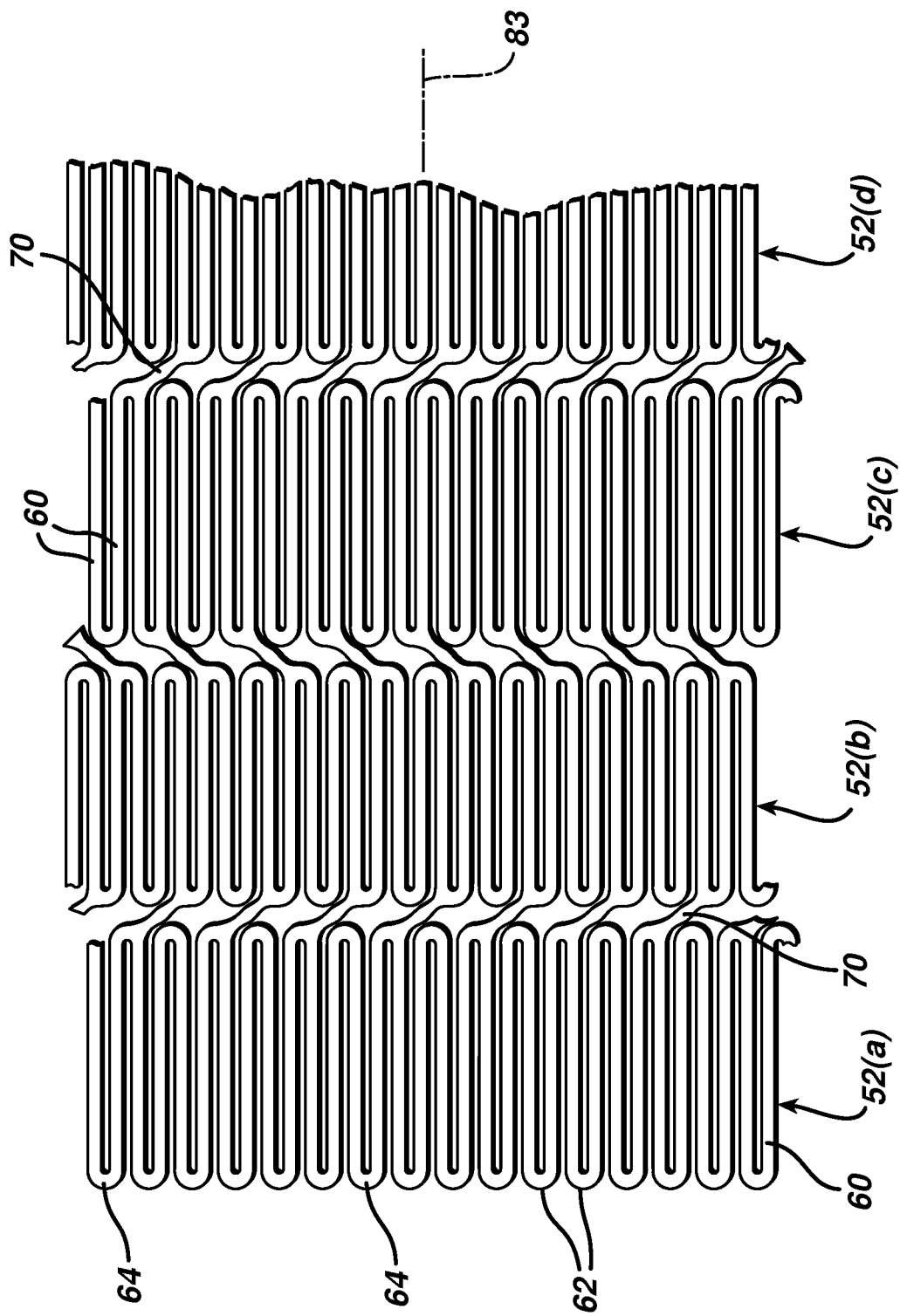
FIG. 4 is a sectional, flat view of the stent shown in FIG. 1.

Referring now to the figures wherein like numerals indicate the same element throughout the views, there is shown in FIGS. 3 and 4, a stent 50 made in accordance with the present invention. FIGS. 3 and 4 show stent 50 in its un-expanded or compressed state. Stent 50 is preferably made from a superelastic alloy such as Nitinol. Most preferably, stent 50 is made from an alloy comprising from about 50.5% (as used herein these percentages refer to atomic percentages) Ni to about 60% Ni, and most preferably about 55% Ni, with the remainder of the alloy Ti. Preferably, the stent is such that it is superelastic at body temperature, and preferably has an Af in the range from about 24.degree. C. to about 37.degree. C. The superelastic design of the stent makes it crush recoverable which, as discussed above, can be used as a stent or frame for any number of vascular devices for different applications.

Figure 4A:
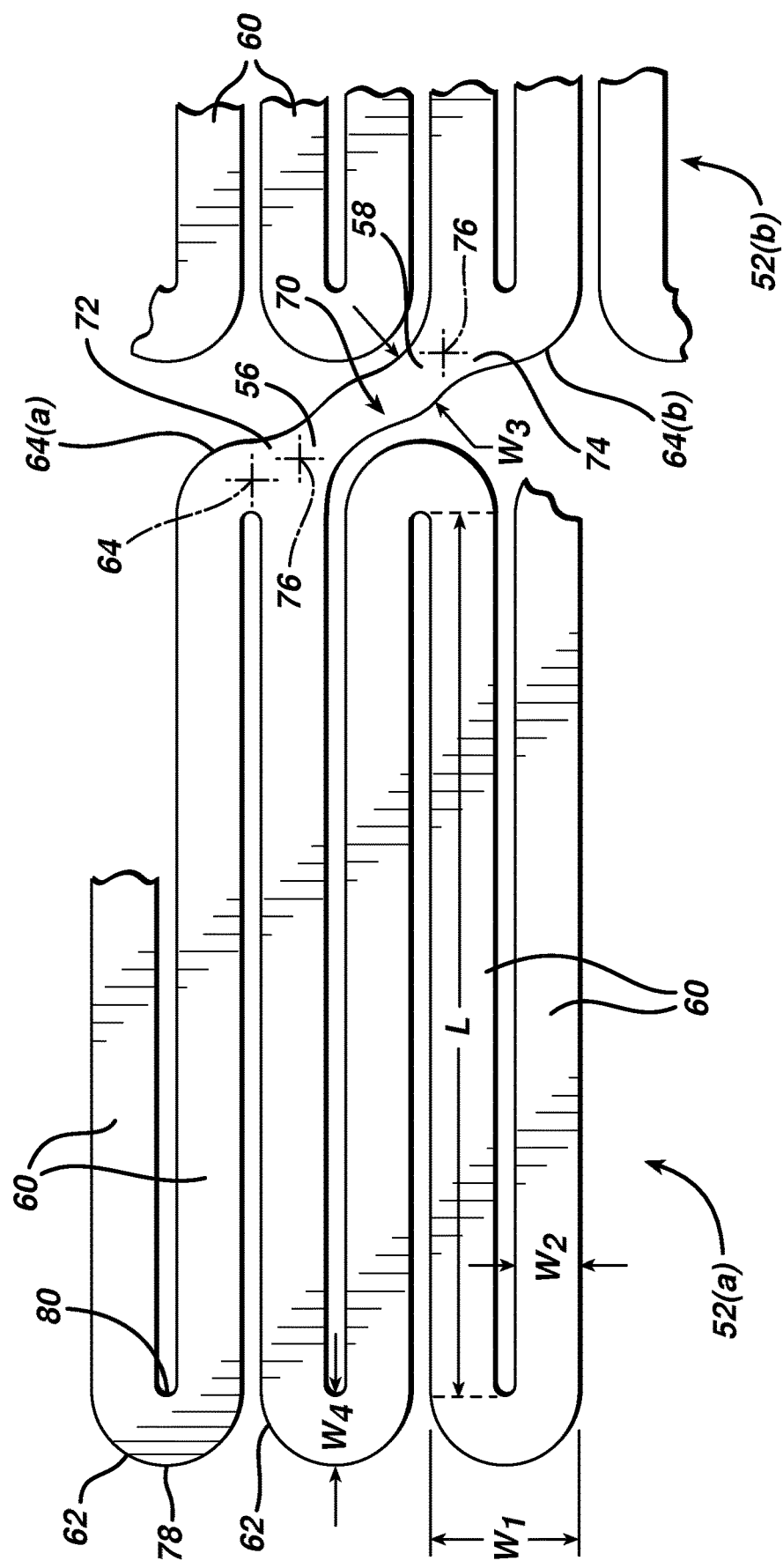
FIG. 4A is an enlarged view of section of the stent shown in FIG. 4.

Stent 50 is a tubular member having front and back open ends 81 and 82 and a longitudinal axis 83 extending therebetween. The tubular member has a first smaller diameter, FIGS. 3 and 4, for insertion into a patient and navigation through the vessels, and a second larger diameter, FIGS. 5 and 6, for deployment into the target area of a vessel. The tubular ember is made from a plurality of adjacent hoops 52, FIG. 4A showing hoops 52(a)-52(b), extending between the front and back ends 81 and 82. The hoops 52 include a plurality of longitudinal struts 60 and a plurality of loops 62 connecting adjacent struts, wherein adjacent struts are connected at opposite ends so as to form a series of peaks 78 and valleys 80 in a substantially S or Z shape pattern. The loops 62 are curved substantially semi-circular and symmetrical sections having centers 64 and a substantially constant radius of curvature in the crimped configuration illustrated in FIG. 4A. The peak 78 and valley 80 are defined as the apex along the outside and inside curve, respectively, of loop member 62.

Stent 50 further includes a plurality of bridges 70 which connect adjacent hoops 52 which can best be described by referring to FIG. 4. Each bridge has two ends 56 and 58. The bridges have one end attached to one strut and/or loop, another end attached to a strut and/or loop on an adjacent hoop. In one embodiment, bridges 70 connect adjacent struts together at bridge to loop connection points 72 and 74. For example, end 56 is connected to loop 64(a) at bridge to loop connection point 72, and end 58 is connected to loop 64(b) at bridge to loop connection point 74. Each bridge to loop connection point has a center 76. The bridge to loop connection points are separated angularly with respect to the longitudinal axis. That is the connection points are not immediately opposite each other. One could not draw a straight line between the connection points, wherein such line would be parallel to the longitudinal axis of the stent.

The above described geometry helps to better distribute strain throughout the stent, prevents metal to metal contact when the stent is bent, and minimizes the opening size between the features, struts loops and bridges. The number of and nature of the design of the struts, loops and bridges are important factors when determining the working properties and fatigue life properties of the stent. Preferably, each hoop has between 24 and 36 or more struts. Preferably the stent has a ratio of number of struts per hoop to strut length L (in inches) which is greater than 200. The length of a strut is measured in its compressed state parallel to the longitudinal axis 83 of the stent.

Figure 5:
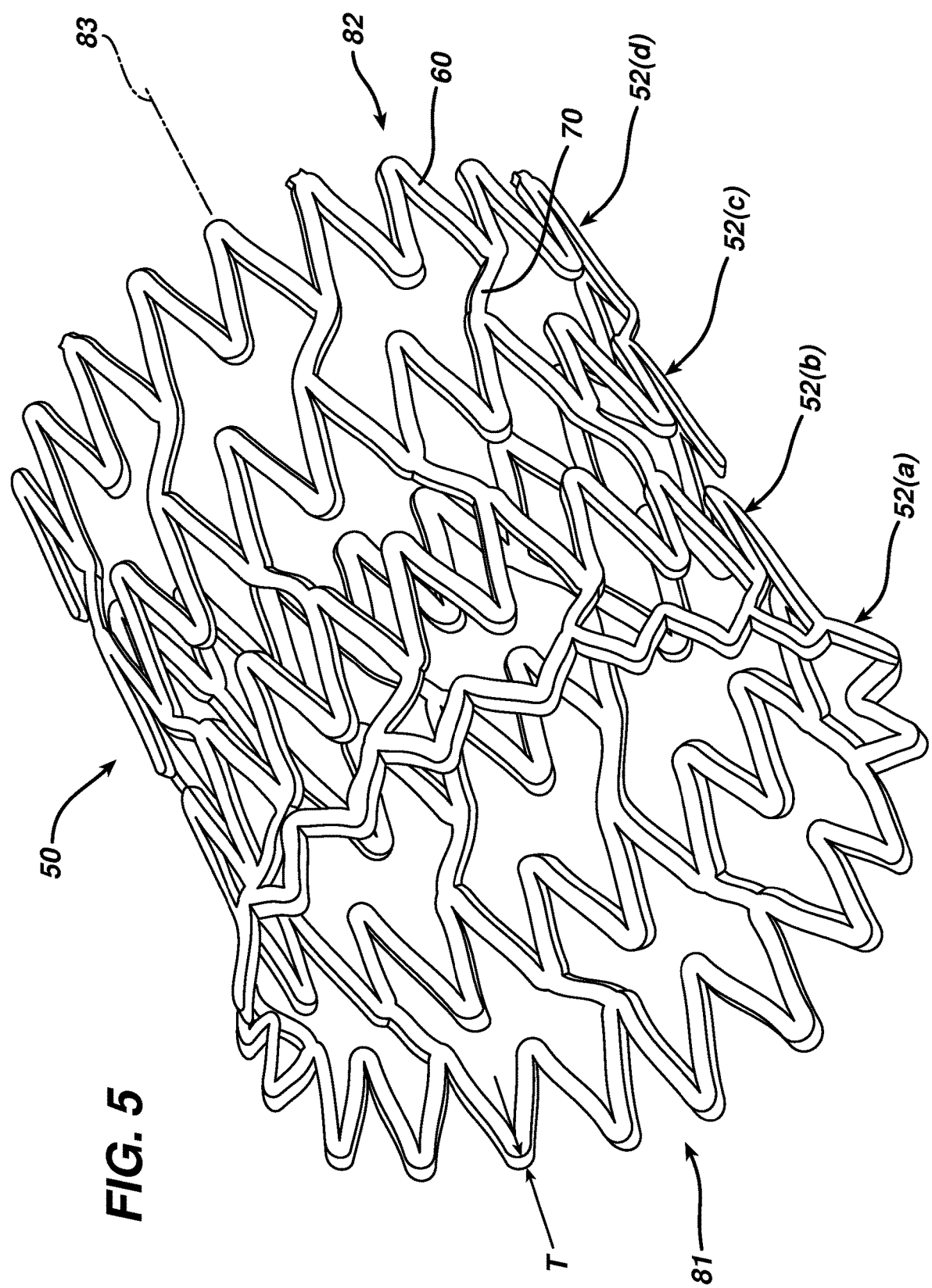
FIG. 5 is a perspective view of the stent shown in FIG. 1 but showing it in its expanded state.
Figure 6:
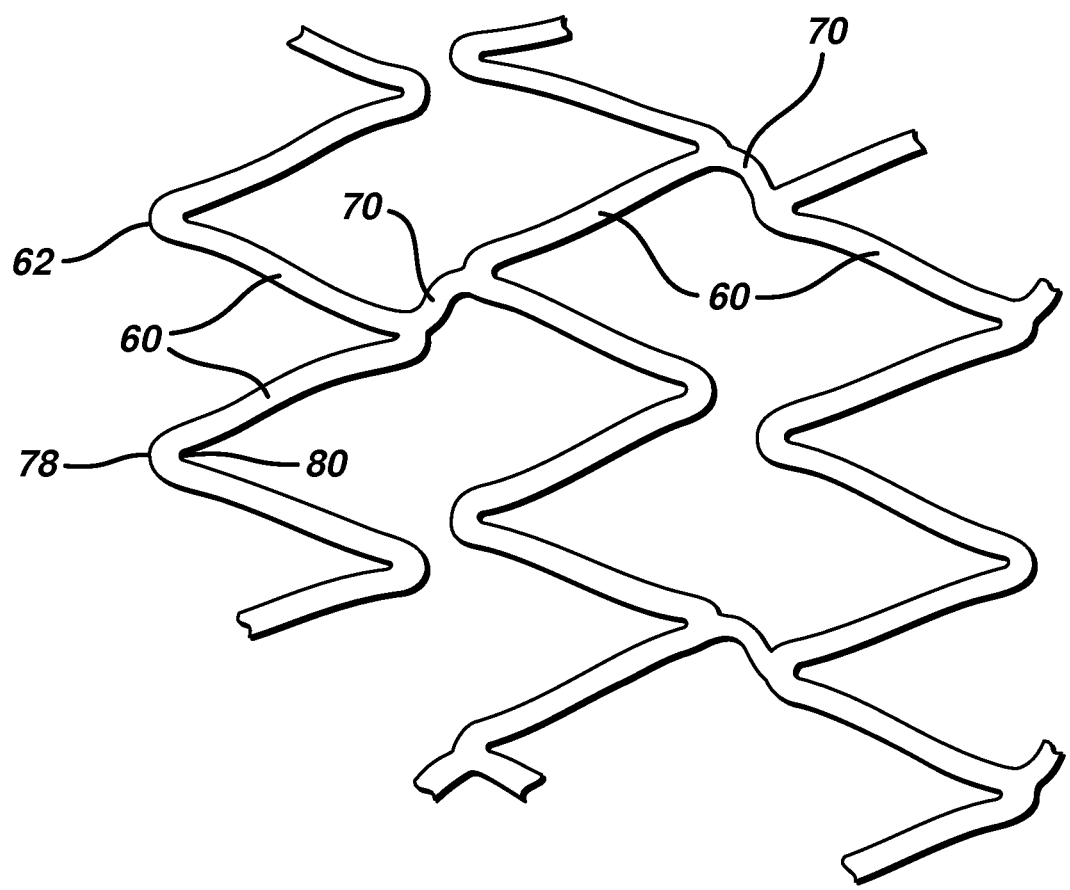
FIG. 6 is an enlarged sectional view of the stent shown in FIG. 5.

As seen from FIGS. 4 and 5, the geometry of the stent changes quite significantly as a stent is deployed from its un-expanded state to its expanded state. As a stent undergoes diametric change, the strut angle and strain levels in the loops and bridges are affected. Preferably, all of the stent features will strain in a predictable manor so that the stent is reliable and uniform in strength. In addition, it is preferable to minimize the maximum strain experienced by struts loops and bridges, since Nitinol properties are more generally limited by strain rather than by stress as most materials are. As will be discussed in greater detail below, the stent sits in the delivery system in its un-expanded state as shown in FIG. 4. As the stent is deployed, it is allowed to expand towards its expanded state, as shown in FIG. 5, which preferably has a diameter which is the same or larger than the diameter of the target vessel. Nitinol stents made from wire deploy in much the same manor and are dependent upon the same design constraints as laser cut stents. Stainless steel stents deploy similarly in terms of geometric changes as they are assisted with forces from balloons or other devices.

In trying to minimize the maximum strain experienced by features, the present invention utilizes structural geometry's which distribute strain to areas of the stent which are less susceptible to failure than others. For example, one of the most vulnerable areas of the stent is the inside radius of the connecting loops. The connecting loops undergo the most deformation of all the stent features. The inside radius of the loop would normally be the area with the highest level of strain on the stent. This area is also critical in that it is usually the smallest radius on the stent. Stress concentrations are generally controlled or minimized by maintaining the largest radii possible. Similarly, we want to minimize local strain concentrations on the bridge and bridge connection points. One way to accomplish this is to utilize the largest possible radii while maintaining feature widths which are consistent with applied forces. Another consideration is to minimize the maximum open area of the stent. Efficient utilization of the original tube from which the stent is cut increases stent strength and its ability to trap embolic material.

Many of these objectives have been accomplished by a preferred embodiment of the present invention, shown in FIGS. 3, 4 and 7A-7F. As seen from these figures, the most compact designs which maintain the largest radii at the loop to bridge connections are non-symmetric with respect to the centerline of the strut connecting loop. That is, loop to bridge connection point centers 76 are offset from the center 64 of the loops 62 to which they are attached. The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improves fatigue life by minimizing local strain levels, allows for smaller open areas which enhance entrapment of embolic material, and improves stent apposition in irregular vessel wall shapes and curves.

As seen in FIG. 4A, stent 50 has strut connecting loops 62 having a width W4, as measured at the center 64 parallel to axis 83, which are greater than the strut widths W2, as measured perpendicular to axis 83 itself In fact it is preferable that the thickness of the loops vary so that they are thickest near their centers This increases strain deformation at the strut and reduces the maximum strain levels at the extreme radii of the loop. This reduces the risk of stent failure and allows us to maximize radial strength properties. The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improves fatigue life by minimizing local strain levels, allows for smaller open areas which enhance entrapment of embolic material, and improves stent apposition in irregular vessel wall shapes and curves.

As mentioned above bridge geometry changes as a stent is deployed from its compressed state to its expanded state and vice-versa. As a stent undergoes diametric change, strut angle and loop strain is affected. Since the bridges are connected to either the loops, struts or both, they are affected. Twisting of one end of the stent with respect to the other, while loaded in the stent delivery system, should be avoided. Local torque delivered to the bridge ends displaces the bridge geometry. If the bridge design is duplicated around the stent perimeter, this displacement causes rotational shifting of the two loops being connected by the bridges. If the bridge design is duplicated throughout the stent, as in the present invention, this shift will occur down the length of the stent. This is a cumulative effect as one considers rotation of one end with respect to the other upon deployment. A stent delivery system, such as the one described below, will deploy the distal end first, and then allow the proximal end to expand. It would be undesirable to allow the distal end to anchor into the vessel wall while holding the stent fixed in rotation, then release the proximal end. This could cause the stent to twist or whip in rotation to equilibrium after it is at least partially deployed within the vessel. Such whipping action could cause damage to the vessel.

However, one embodiment of the present invention, as shown in FIGS. 3 and 4, reduces the chance of such events from happening when deploying the stent. By mirroring the bridge geometry longitudinally down the stent, the rotational shift of the Z-sections can be made to alternate and will minimize large rotational changes between any two points on a given stent during deployment or constraint. That is the bridges connecting loop 52(b) to loop 52(c) are angled upwardly from left to right, while the bridges connecting loop 52(c) to loop 52(d) are angled downwardly from left to right. This alternating pattern is repeated down the length of the stent. This alternating pattern of bridge slopes improves the torsional characteristics of the stent so as to minimize any twisting or rotation of the stent with respect to any two hoops. This alternating bridge slope is particularly beneficial if the stent starts to twist in vivo. As the stent twists, the diameter of the stent will change. Alternating bridge slopes tend to minimize this effect. The diameter of a stent having bridges which are all sloped in the same direction will tend grow if twisted in one direction and shrink if twisted in the other direction. With alternating bridge slopes this effect is minimized and localized.

The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improves fatigue life by minimizing local strain levels, allows for smaller open areas which enhance entrapment of embolic material, and improves stent apposition in irregular vessel wall shapes and curves.

Preferably, stents are laser cut from small diameter tubing. For prior art stents, this manufacturing process lead to designs with geometric features, such as struts, loops and bridges, having axial widths W2, W4 and W3 (respectively) which are larger than the tube wall thickness T (shown in FIG. 5). When the stent is compressed, most of the bending occurs in the plane that is created if one were to cut longitudinally down the stent and flatten it out. However, for the individual bridges, loops and struts, which have widths greater than their thickness, they have a greater resistance to this in-plane bending than they do to out of plane bending. Because of this, the bridges and struts tend to twist, so that the stent as a whole can bend more easily. This twisting is a buckling condition which is unpredictable and can cause potentially high strain.

However, this problem has been solved in the preferred embodiment of the present invention, shown in FIGS. 3 and 4. As seen from these figures, the widths of the struts, hoops and bridges are equal to or less than the wall thickness of the tube. Therefore, substantially all bending and, therefore, all strains are "out of plane". This minimizes twisting of the stent which minimizes or eliminates buckling and unpredictable strain conditions. The feature is particularly advantageous for stents having large expansion ratios, which in turn requires them to have extreme bending requirements where large elastic strains are required. Nitinol can withstand extremely large amounts of elastic strain deformation, so the above features are well suited to stents made from this alloy. This feature allows for maximum utilization of Ni—Ti or other material capabilities to enhance radial strength, improve stent strength uniformity, improves fatigue life by minimizing local strain levels, allows for smaller open areas which enhance entrapment of embolic material, and improves stent apposition in irregular vessel wall shapes and curves.

A number of approaches have been used to add flexibility and durability to basic stent design for indications having loading modalities involving dynamic bending, torsion, and axial extension/compression. Prior concepts, which reduced the number of bridges specified in the standard stent designs have shown excellent flexibility, but have axial instability, resulting in problematic catheterization and deployment characteristics. The present invention is directed towards maintaining the advantages associated with fewer bridges between hoops while providing a structural element that leaves enough axial constraint between hoops to provide stability during the catheterization and deployment processes. By lengthening the bridge relative to the length of the struts forming the individual hoops, the bridge provides necessary constraint between adjacent hoops while simultaneously providing the capability to absorb some of the deformation associated with torsion, bending and axial extension/compression. In addition, the width of the bridge along its length may be "tuned" to maximize the balance between flexibility and cyclic deformation such that durability may be optimized while still tolerating the presence of non-radial forces within the stent structure.

One alternate embodiment of the present invention that adds this flexibility while still maintain axial constraint and stability is shown in FIGS. 7A through 7F. FIGS. 7A through 7F show stent 150 which is similar to stent 50 shown in the previous drawings. Stent 150 is made from a plurality of adjacent hoops 152, FIGS. 7A through 7F show hoops 152(*a*)-152(*d*). The hoops 152 include a plurality of longitudinal struts 160 and a plurality of loops 162 connecting adjacent struts, wherein circumferentially adjacent struts are connected at opposite ends so as to form series of peaks or apices and valleys in an S or Z shape pattern. Stent 150 further includes a plurality of bridges 170 which connect adjacent hoops 152 at bridge to loop connection points. As seen from FIGS. 7A-F and FIGS. 8A-B, bridges 170 incorporate elongated linear strut sections 175 connected on each end to a first end of a curved bridge loop members 180. The second end of the curved loop member 180 is connected to the adjacent hoop 152 at the bridge to loop connection point. In a one embodiment, the curved loop member 180 is attached to the loop 162 of the adjacent hoop 152.

In a preferred embodiment, the ratio of the circumference of the hoop 152 to the length of the elongated linear strut member 175 is less than 5.

Each bridge 170 is sized to span a plurality of loops 162 between the connection points on adjacent hoops 152. The configuration provides additional structural stability in the open area between adjacent hoops 152. The elongated bridge members 170 may be designed to approximate the mechanical behavior of a helical spring coil. The result is a stent 150 that has repeating hoop sections 152 for radial strength, and bridge sections 170 that provide needed flexibility under bending and axial/torsional loading conditions.

Individual hoops 152 tend to be unstable when deformed by typical catheterization and deployment forces, so the connection point between the bridge 170 and the hoops 152 are located to avoid creating large areas of axially unconstrained strut apices. In a preferred embodiment, the ratios of the hoop circumference to the distance between the adjacent hoops is between 20:1 and 50:1, and preferably about 25:1.

Figure 7D:
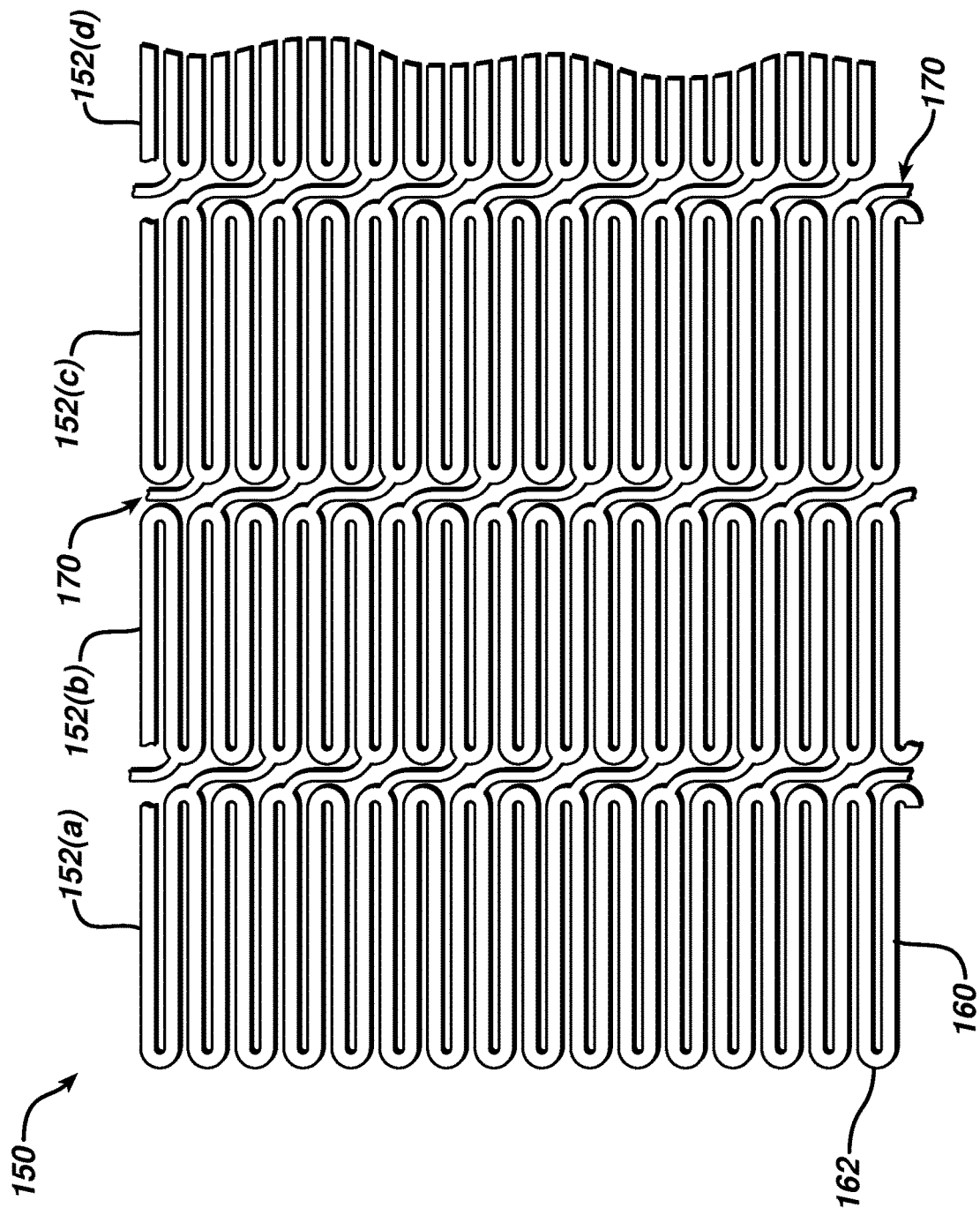
FIG. 7D is a view similar to that of FIG. 4 but showing an alternative embodiment of the present invention.
Figure 7E:
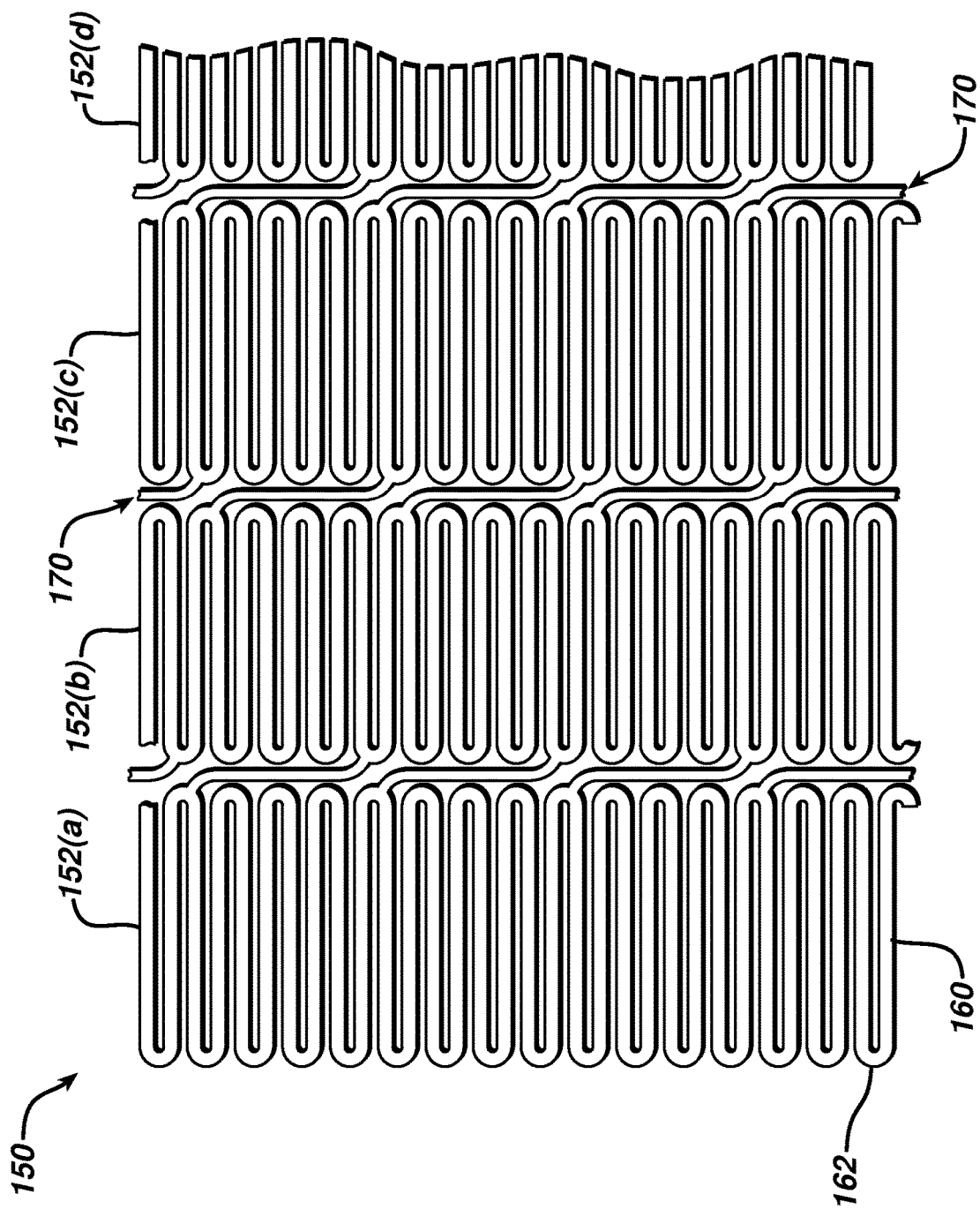
FIG. 7E is a view similar to that of FIG. 4 but showing an alternative embodiment of the present invention.

In a preferred embodiment the connection point between the bridge 170 and the hoops 152 will have a repeating pattern over a plurality of loops 162 such that the benefits of a decreased number of bridges 170 is realized while simultaneously avoiding the creation of overly unconstrained hoops 152. It is preferred that the ratio of total number of loops 162 per side (proximal or distal) of the hoop 152 to the number of loops 162 (per side) having connection regions (also spanned by a particular bridge 170) for the given hoop 152 be a whole number. For example, FIGS. 7A-F depict a stent having 16 loops 162 per side of the hoop 152. A preferred embodiment would have 8, 4 or 2 connection regions (i.e. bridge 170 would span 2, 4, or 8 loops 162) on the given side and maintain symmetry. The selected ratio should be chosen to maximize flexibility and structural stability. FIG. 7A depicts a stent having 16 loops 162 per side of the hoop 152 with a total of 8 bridges (8 connection regions per side), each spanning 2 loops 162. FIG. 7B depicts a stent having 16 loops 162 per side of hoop 152 with a total of 4 bridges (4 connection regions per side), each spanning 4 loops 162. FIG. 7C depicts a stent having 16 loops 162 per side of hoop 152 with a total of 2 bridges (2 connection regions per side), each spanning 8 loops 162. FIGS. 7A-C depict adjacent hoops 152 to be in axial alignment. That is each loop 162 on each hoop 152 is in the same orientation relative to the longitudinal axis. However, the loops 162 on adjacent hoops 152 may rotationally offset, i.e. not in axial alignment to provide longer struts and added flexibility. The stents 150 depicted in FIGS. 7D-F illustrate hoop sections 152 that are rotationally offset from the adjacent hoop section 152. In particular, this rotational offset is equal to a 180 degree phase shift, yielding adjacent hoops 152 that are a mirror image of one another.

Figure 8A:
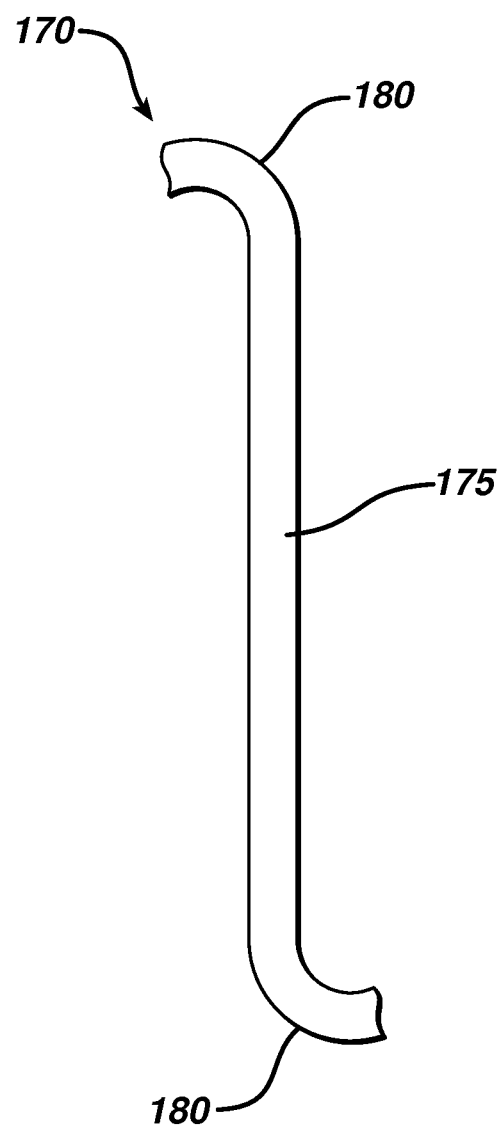
FIG. 8A is an enlarged view of a bridge member according to one embodiment of the present invention.
Figure 8B:
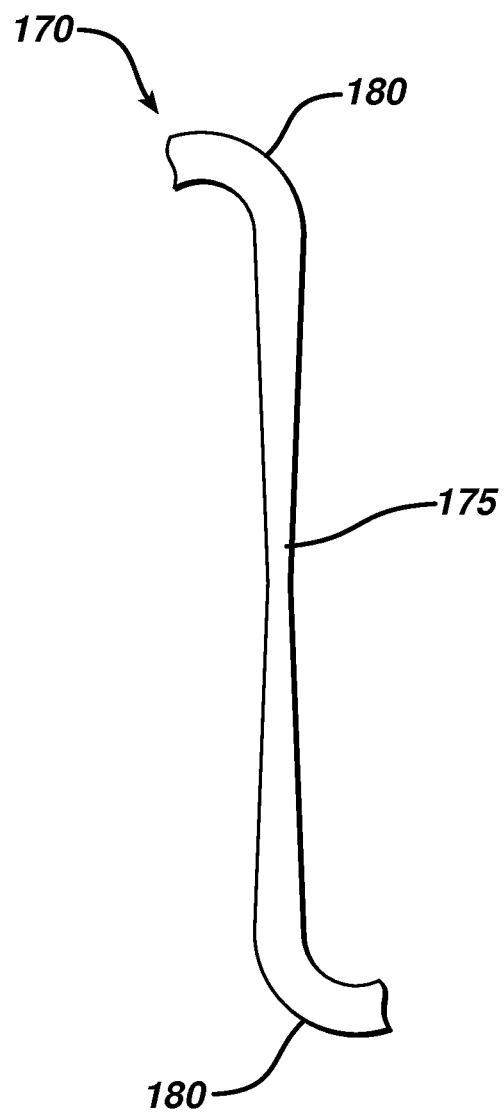
FIG. 8B is an enlarged view of a bridge member according to one embodiment of the present invention.

The width of the elongated linear strut section 175 may vary along its length, preferably being symmetrical about its center to avoid non-uniform deflection characteristics. The connection point between the bridge 170 and hoops 152 is likely to form a natural hinge point under deflection. In a preferred embodiment, the bridge 170 width at the connection point to the hoop 152 will be optimized such that fatigue durability is reasonably maintained. To achieve this optimization, the bridge 170 width at the connection point will be wider than other points along the length of the bridge 170. The bridge 170 shape and width may be further optimized to reduce out-of-plane forces that develop as a result of torsion, e.g. a bridge 170 may have its narrowest point at its center (relative to its length) to reduce the amount of torsional distortion transmitted between hoops 152. FIG. 8B illustrates a bridge 170 having a tapered elongated linear strut section 175 with the narrowest point at the center point along its length.

As mentioned above, it is preferred that the stent of the present invention be made from a superelastic alloy and most preferably made of an alloy material having greater than 50.5 atomic % Nickel and the balance titanium. Greater than 50.5 atomic % Nickel allows for an alloy in which the temperature at which the martensite phase transforms completely to the austenite phase (the Af temperature) is below human body temperature and preferably is about 24.degree. C. to about 37.degree. C. so that austenite is the only stable phase at body temperature.

In manufacturing the Nitinol stent, the material is first in the form of a tube. Nitinol tubing is commercially available from a number of suppliers including Nitinol Devices and Components, Fremont Calif. The tubular member is then loaded into a machine which will cut the predetermined pattern of the stent, which was discussed above and is shown in the figures, into the tube. Machines for cutting patterns in tubular devices to make stents or the like are well known to those of ordinary skill in the art and are commercially available. Such machines typically hold the metal tube between the open ends while a cutting laser, preferably under microprocessor control, cuts the pattern. The pattern dimensions and styles, laser positioning requirements, and other information are programmed into a microprocessor which controls all aspects of the process. After the stent pattern is cut, the stent is treated and polished using any number of methods well known to those skilled in the art. Lastly, the stent is then cooled until it is completely martensitic, crimped down to its un-expanded diameter and then loaded into the sheath of the delivery apparatus.

It is believed that many of the advantages of the present invention can be better understood through a brief description of a delivery apparatus for the stent, as shown in FIGS. 1 and 2. FIGS. 1 and 2 show a self-expanding stent delivery apparatus I for a stent made in accordance with the present invention. Apparatus I comprises inner and outer coaxial tubes. The inner tube is called the shaft 10 and the outer tube is called the sheath 40. Shaft 10 has proximal and distal ends 12 and 14 respectively. The distal end 14 of the shaft terminates at a luer lock hub 5. Preferably, shaft 10 has a proximal portion 16 which is made from a relatively stiff material such as stainless steel, Nitinol, or any other suitable material, and an distal portion 18 which is made from a polyethylene, polyimide, pellethane, Pebax, Vestamid, Cristamid, Grillamid or any other suitable material known to those of ordinary skill in the art. The two portions are joined together by any number of means known to those of ordinary skill in the art. The stainless steel proximal end gives the shaft the necessary rigidity or stiffness it needs to effectively push out the stent, while the polymeric distal portion provides the necessary flexibility to navigate tortuous vessels.

The distal portion 18 of the shaft has a distal tip 20 attached thereto. The distal tip 20 has a proximal end 34 whose diameter is substantially the same as the outer diameter of the sheath 40. The distal tip tapers to a smaller diameter from its proximal end to its distal end, wherein the distal end 36 of the distal tip has a diameter smaller than the inner diameter of the sheath. Also attached to distal portion 18 of shaft 10 is a stop 22 which is proximal to the distal tip 20. Stop 22 can be made from any number of materials known in the art, including stainless steel, and is even more preferably made from a highly radiopaque material such as platinum, gold tantalum. The diameter of stop 22 is substantially the same as the inner diameter of sheath 40, and would actually make frictional contact with the inner surface of the sheath. Stop 22 helps to push the stent out of the sheath during deployment, and helps the stent from migrating proximally into the sheath 40.

A stent bed 24 is defined as being that portion of the shaft between the distal tip 20 and the stop 22. The stent bed 24 and the stent 50 are coaxial so that the portion of shaft 18 comprising the stent bed 24 is located within the lumen of the stent 50. However, the stent bed 24 does not make any contact with stent 50 itself. Lastly, shaft 10 has a guidewire lumen 28 extending along its length from its proximal end 12 and exiting through its distal tip 20. This allows the shaft 10 to receive a guidewire much in the same way that an ordinary balloon angioplasty catheter receives a guidewire. Such guidewires are well known in art and help guide catheters and other medical devices through the vasculature of the body.

Sheath 40 is preferably a polymeric catheter and has a proximal end 42 terminating at a hub 52. Sheath 40 also has a distal end 44 which terminates at the proximal end 34 of distal tip 20 of the shaft 18, when the stent is in its fully un-deployed position as shown in the figures. The distal end 44 of sheath 40 includes a radiopaque marker band 46 disposed along its outer surface. As will be explained below, the stent is fully deployed when the marker band 46 is lined up with radiopaque stop 22, thus indicating to the physician that it is now safe to remove the apparatus I from the body. Sheath 40 preferably comprises an outer polymeric layer and an inner polymeric layer. Positioned between outer and inner layers a braided reinforcing layer. Braided reinforcing layer is preferably made from stainless steel. The use of braided reinforcing layers in other types of medical devices can be found in U.S. Pat. No. 3,585,707 issued to Stevens on Jun. 22, 1971, U.S. Pat. No. 5,045,072 issued to Castillo et al. on Sep. 3, 1991, and U.S. Pat. No. 5,254,107 issued to Soltesz on Oct. 19, 1993, all of which are hereby incorporated herein by reference.

FIGS. 1 and 2 show the stent 50 as being in its fully un-deployed position. This is the position the stent is in when the apparatus 1 is inserted into the vasculature and its distal end is navigated to a target site. Stent 50 is disposed around stent bed 24 and at the distal end 44 of sheath 40. The distal tip 20 of the shaft 10 is distal to the distal end 44 of the sheath 40, and the proximal end 12 of the shaft 10 is proximal to the proximal end 42 of the sheath 40. The stent 50 is in a compressed state and makes frictional contact with the inner surface 48 of the sheath 40.

When being inserted into a patient, sheath 40 and shaft 10 are locked together at their proximal ends by a Touhy Borst valve 8. This prevents any sliding movement between the shaft and sheath which could result in a premature deployment or partial deployment of the stent. When the stent 50 reaches its target site and is ready for deployment, the Touhy Borst valve 8 is opened so that that the sheath 40 and shaft 10 are no longer locked together.

The method under which apparatus 1 deploys stent 50 should be readily apparent. The apparatus 1 is first inserted into a vessel so that the stent bed 24 is at a target diseased site. Once this has occurred the physician would open the Touhy Borst valve 8. The physician would then grasp the proximal end 12 of shaft 10 so as to hold it in place. Thereafter, the physician would grasp the proximal end 42 of sheath 40 and slide it proximal, relative to the shaft 40. Stop 22 prevents the stent 50 from sliding back with the sheath 40, so that as the sheath 40 is moved back, the stent 50 is pushed out of the distal end 44 of the sheath 40. Stent deployment is complete when the radiopaque band 46 on the sheath 40 is proximal to radiopaque stop 22. The apparatus I can now be withdrawn through stent 50 and removed from the patient.

Although particular embodiments of the present invention have been shown and described, modification may be made to the device and/or method without departing from the spirit and scope of the present invention. The terms used in describing the invention are used in their descriptive sense and not as terms of limitations.

What is claimed is:

1. A stent for insertion into a vessel of a patient, said stent comprising:

a tubular member with front and back open ends and a longitudinal axis extending there between, said member having a first smaller diameter for insertion into said vessel, and a second larger diameter for deployment into said vessel, said tubular member comprising a plurality of at least three adjacent hoops each having proximal and distal open ends relative to the longitudinal axis, said adjacent hoops comprising a plurality of longitudinal struts and a plurality of loops connecting circumferentially adjacent struts so as to form a series of peaks and valleys in a substantially S or Z shaped pattern; and a plurality of bridges connected between loops on said adjacent hoops in a repeating pattern, wherein each bridge comprises an elongated linear strut member having an arcuate first end and an arcuate second end with a no curve portion along a majority of bridge length between the first and second arcuate ends, the linear strut member extending perpendicularly to the longitudinal axis and directly connected to a first connection region on a first curved bridge loop member of a first hoop and to a second connection region on a radially offset second curved bridge loop member of an adjacent hoop, such that a first bridge of the plurality of bridges connects a first adjacent hoop to an adjacent second hoop and is parallel to a second bridge of the plurality of bridges that connects the adjacent second hoop to an adjacent third hoop so as to approximate the mechanical behavior of a helical spring coil, wherein the ratio of the circumference of the tubular member to the length of the elongated linear strut member is less than 5.

2. The stent according to claim 1 wherein the repeating pattern is a ratio of the total number of loops for a given end of one of the adjacent hoops to the number of connection regions for the same end of the same hoop, and wherein the ratio is a whole number.

3. The stent according to claim 2 wherein the ratio is 4:1.

4. The stent according to claim 2 wherein the ratio is 8:1.

5. The stent according to claim 2 wherein the ratio is 2:1.

6. The stent according to claim 1 wherein the loops on adjacent hoops are longitudinally aligned but oppositely oriented relative to the longitudinal axis.

7. The stent according to claim 1 wherein the immediately opposite loops on adjacent hoops are rotationally off-set relative to the longitudinal axis.

8. The stent according to claim 5 wherein the whole number is an even number.

9. The stent according to claim 1 wherein the bridges are evenly spaced along the circumference of the tubular member.

10. The stent according to claim 1 wherein the ratio of the circumference of the tube to the distance between the adjacent hoops is between 20:1 and 50:1.

11. The stent according to claim 1 wherein said stent is made from a superelastic alloy.

12. The stent according to claim 11 wherein said alloy comprises from about 50.5 percent to about 60 percent Nickel and the remainder comprising Titanium.

13. The stent according to claim 5 wherein said elongated linear strut member is tapered with the narrowest point at the center point along its length.

* * * * *